(12) United States Patent
Bertola

(10) Patent No.: US 6,191,322 B1
(45) Date of Patent: Feb. 20, 2001

(54) PROCESS FOR THE PRODUCTION OF BUTANEDIOL BY LIQUID PHASE HYDROGENATION

(75) Inventor: Aldo Bertola, Milan (IT)

(73) Assignee: Pantochim S.A., Feluy (BE)

(*) Notice: Under 35 U.S.C. 154(b), the term of this patent shall be extended for 0 days.

(21) Appl. No.: 09/367,038

(22) PCT Filed: Jan. 5, 1999

(86) PCT No.: PCT/EP99/00016
  § 371 Date: Aug. 6, 1999
  § 102(e) Date: Aug. 6, 1999

(87) PCT Pub. No.: WO99/35114
  PCT Pub. Date: Jul. 15, 1999

(30) Foreign Application Priority Data

Jan. 8, 1998 (BE) .................................................. 9800011

(51) Int. Cl.$^7$ ................................................. C07C 29/132
(52) U.S. Cl. ............................................. 568/864; 54/508
(58) Field of Search ............................. 568/864; 549/508

(56) References Cited

U.S. PATENT DOCUMENTS

| | | | |
|---|---|---|---|
| 2,079,414 | 5/1937 | Lazier | 260/156 |
| 3,772,395 | 11/1973 | Yamaguchi et al. | 260/635 D |
| 4,613,707 | 9/1986 | Kouba et al. | 568/864 |
| 4,652,685 | 3/1987 | Cawse et al. | 568/864 |
| 4,751,334 | 6/1988 | Turner et al. | 568/864 |
| 5,334,779 | * 8/1994 | Kuo et al. | 568/864 |

FOREIGN PATENT DOCUMENTS

| | | |
|---|---|---|
| 892958 | 8/1982 | (BE) . |
| 2144316 | 3/1972 | (DE) . |
| 0382050 | 8/1990 | (EP) . |
| 3903363 | 8/1990 | (DE) . |
| 400567 | 10/1973 | (RU) . |

\* cited by examiner

*Primary Examiner*—Peter O'Sullivan
(74) *Attorney, Agent, or Firm*—Stevens, Davis, Miller & Mosher, LLP

(57) ABSTRACT

Process for the production of 1,4-butanediol by mixed phase catalytic hydrogenation of gamma-butyrolactone, succinic anhydride esters, or mixtures thereof.

14 Claims, 1 Drawing Sheet

PROCESS FOR THE PRODUCTION OF BUTANEDIOL BY LIQUID PHASE HYDROGENATION

Figure 1:
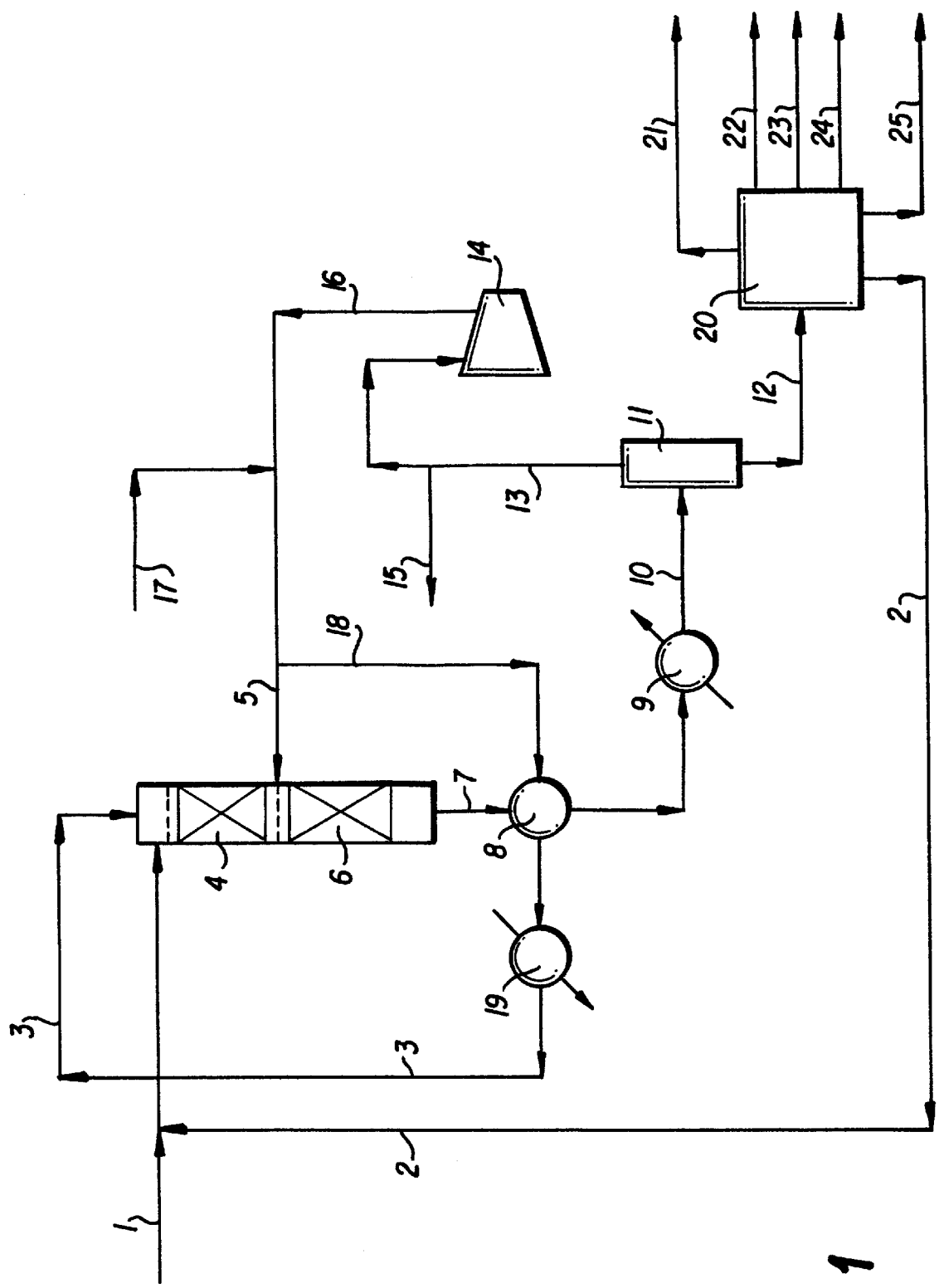

This application is a 371 of PCT/EP99/00016 filed Jan. 5, 1999.

DESCRIPTION

The present invention relates to a process for the production of 1,4-butanediol, and particularly it relates to the employment of mixed phase flow catalytic hydrogenation of gamma-butyrolactone, succinic anhydride esters, or mixtures thereof.

It is known from the prior art that there exist several processes for production of 1,4 butanediol (BDO) from dicarboxylic acid esters with four carbon atoms as starting materials.

In USSR Patent No. 400,567 a copper chromite catalysed liquid phase conversion of esters into BDO at temperatures ranging between 280 and 300° C. and 300 bar pressure is given.

In U.S. Pat. No. 4,613,707 a conversion of diethylsuccinate into BDO at 200° C. T and 135 bar pressure with a mainly copper and aluminium borate catalyst is given.

In U.S. Pat. No. 2,079,414 a vapour phase hydrogenation of esters is given, on a copper chromite type catalyst and temperatures ranging between 300 and 400° C.

In U.S. Pat. No. 204,944 a broad description of both liquid and vapour phase ester hydrogenations is given, using copper chromite catalysts. In one example, a liquid phase butyl succinate hydrogenation at 207 bars is described.

In U.S. Pat. Nos. 4,584,419 and 4,751,334, owned by Davy Mc Kee Ltd. (U.K.) processes for the large scale production of BDO are described, wherein 4 carbon dicarboxylic acid hydrogenations are resorted to.

In the above processes, the hydrogenation rections take place in two sequential stages in the vapour phase, and in the presence of a copper chromite type hydrogenation catalyst.

According to the processes assigned to Davy Mc Kee Ltd., each of the two hydrogenation stages occurs in the conditions ranging between the following values:

Pressure: between 25 and 70 bars

Temperature: between 150° and 200° C.

$H_2$/ester ratio: between 100/1 and 800/1

1,4-butanediol synthesis from gammabutyrolactone (GBL) is mentioned in German Patent No. 2,144,316, assigned to Mitsubishi Corporation of Japan. Conversion is carried out on a nickel-cobalt catalyst, at temperatures between 200 and 250° C. and pressures between 100 and 120 bars.

In Belgian Patent No. 892,958 a vapour phase hydrogenation process of GBL to BDO is given, at pressures between 15 and 30 bars, and temperatures ranging between 200 and 230° C., on a copper-zinc oxide based catalyst.

In U.S. Pat. No. 4,652,685 a similar process is described, and this is carried out in the vapour phase and at 40 bar pressure, 210° C. and on a barium stabilised copper chromite type catalyst.

In German Patent No. 3,903,563 a process is described wherein reaction pressure is 60 bars and a cobalt-copper catalyst is employed.

The conditions to maintain vapour or mixed flow conditions being strictly necessary, all solutions so far proposed for a process for the production of 1,4-butanediol present two types of problems both of which considerably affect costs.

One relates to the large amount of hydrogen needed, more so if compared with the actual amount of this gas which goes to react with the starting material; the other stems from the need to reduce the catalyst before use, operation which is also time consuming, as it entices an at times long phase prior to the process itself.

It is therefore an aim of the present invention to propose a process for the production of 1,4-butanediol which is speedy and cost effective as in this catalysts in their unreduced forms are used, and a very much smaller amount of $H_2$ is used than in anyone of the processes objects of the patents and methodologies in the prior art.

Such aims are accomplished by a process for the production of butanediol by selective catalytic hydrogenation of gamma-butyrolactone, succinic anhydride esters or mixtures of gamma butyrolactone and succinic anhydride esters, characterised by the fact that it occurs in at least two catalytic stages at a pressure ranging between 60 and 100 bars and temperature ranging between 160 and 250° C. which are characterised with the presence of a liquid phase at the entrance of the first stage.

These and other features will be more readily apparent from the following description of a preferred not limiting embodiment of the invention with reference to the accompanying drawing in which a scheme of the production process is shown.

In the process object of the present invention, BDO production takes place starting from GBL, succinic acid esters or mixtures thereof which are mixed phase flow hydrogenated in the presence of suitable hydrogenation catalysts, and at reaction pressure and temperature, using those catalysts that allow high yields and selectivity.

The process object of the present invention results to be more advantageous, with respect to all those processes for the production of butanediol where the hydrogenation is carried out in the vapour phase, as in this smaller hydrogen volumes are required and nevertheless a higher selectivity and conversion can be achieved.

Furthermore, the large scale reactions are carried out at temperatures and pressures that allow remarkable savings when compared with the processes described in the literature mentioned above.

Moreover, this process results to be particularly advantageous if it is associated with a GBL production process which starts from maleic or succinic anhydride esters. In fact, in the GBL production process, together with GBL, an azeotropic mixture consisting of GBL and an unconverted succinic acid ester, dimethylsuccinate (DMS) for instance, is produced. Such a mixture is a nearly ideal starting material in the process which is object of the present invention.

The process object of the present invention is valid even just using a succinic acid ester, namely DMS for example, as starting material. This can be obtained by hydrogention of the corresponding maleic anhydride ester.

The catalysts employed are of the copper-zinc oxide type, all in the non-reduced form, consisting of 20–35% copper, and 25–40% zinc, with a surface area which is not any lower than 30 $m^2g^{-1}$.

Likewise, copper chromite catalysts can be employed, these containing from 40 to 50% copper oxide, from 40 to 50% chromium oxide, from 5 to 15% barium or manganese oxide, with a surface area which is not any lower than 20 $m^2g^{-1}$.

To achieve temperature control in the reaction, it is better to let the reaction occur in at least two stages, allowing for cooling down the fluid between the two stages with a cold hydrogen supply.

The molar ratio between hydrogen and shot at the entrance of the first stage is between 10 and 100, preferably between 20 and 60, while at the entrance of stage two it is between 30 and 150, preferably between 50 and 100.

The overall space velocity measured on a liquid base, is between 0.1 and 1.0 $hr^{-1}$, preferably between 0.2 and 0.4 $hr^{-1}$.

The operating pressure in the process ranges between 60 and 100 bars, preferably between 75 and 90 bars.

The operating temperature of the reaction in the process ranges between 160 and 250° C., preferably between 200° and 220° C.

A scheme of the process is shown in the enclosed drawing. The operating parameters given refer to a starting material consisting of a GBL and DMS mixture, in the 70:30 ratio. The loading mixture (line 1) and a recycled liquid stream containing GBL from fractionation unit 20 (line 2), is mixed with a preheated hydrogen stream (line 3), and fed to a liquid vapour distributor which is placed higher than first reaction stage 4. At the end of the first reaction stage 4 the outgoing liquid-vapour mixture is cooled by cold hydrogen injection (line 5), and goes to feed the following reaction stage 6, after flowing through another liquid-vapour distributor. The overall reaction conditions and performances are the following:

| | |
|---|---|
| Pressure: | 80 bar |
| Temperature: | 180–220° C. |
| Molar Ratio $H_2$: shot (I stage): | 30 |
| Molar Ratio $H_2$: shot (2 stage) | 80 |
| Catalyst: | copper-zinc oxide |
| Liquid Hourly Space Velocity (LHSV): | 0.35 $hr^{-1}$ |
| DMS Conversion | 98% |
| GBL Conversion | 90% |
| Selectivity: | |
| Butanediol | 90.5 % mol |
| Tetrahydrofuran | 9.0% mol |
| Butanol and other byproducts | 0.5% mol |

The effluent from the reactor (Line 7) cools down in the exchanger 8, giving heat to the recycled hydrogen rich stream, and in exchanger 9 after that, and ends up feeding separator 1 (Line 10) where a liquid organic phase separates from a hydrogen rich gaseous phase. The gaseous phase from separator 1 (Line 13) is compressed by compressor 14, and is then recycled to the reaction cycle. A fraction of the recycled gas is purged (Line 15) to avoid excessive deposition of inert material.

Compressed gas (Line 16) together with the hydrogen feedstock (Line 17) partly (line 5) mixes with the effluents from reaction stage 1 and partly (line 18) preheats in exchanger 8 and heater 19, to feed reaction stage 1 (4), together with the shot (line 1) and the recycled material (line 2).

The liquid organic phase from separator 11 feeds (line 12) fractionation unit 20, where an unconverted GBL rich recycle stream (line 2), THF (line 21), methanol (line 22), water and light organic byproducts (line 23), heavy organic by-products (line 24), and BDO (line 25) separate. The process allows production of BDO and partly of THF in a simple and cost effective way, and with great operational flexibility. The process makes BDO, and partly THF production possible.

The cost effectiveness of the present process is especially emphasised in case the BDO production unit described with the process object of the present invention, is integrated with a GBL and THF production unit wherein starting materials are maleic anhydride esters.

What is claimed is:

1. Process for the production of butanediol comprising selective catalytic hydrogenation of gammabutyrolactone, succinic anhydride esters or mixtures of gamma butyrolactone and succinic anhydride esters in at least two successive catalytic steps at a pressure ranging between 60 and 100 bars and temperature ranging between 160 and 250° C., and wherein a liquid phase is present at the entrance of the first stage.

2. A process according to claim 1 wherein the reaction is carried out operating at a pressure ranging between 75 and 90 bars, and temperature ranging between 200 and 220° C.

3. A process according to claim 1, wherein the molar ratio between hydrogen and shot at the first stage ranges between 10 and 100, and the molar ratio between hydrogen and shot in the following one or more stages ranges between 30 and 150.

4. A process according to claim 3, wherein the reaction is carried out at a molar ratio between hydrogen and shot which ranges between 20 and 60 at the entrance of the first stage, and between 50 and 100 at the entrance of the following one or more stages.

5. A process according to claim 1, wherein reaction temperature of the reaction is controlled cooling down the fluid between the reaction stages by supplying cold hydrogen.

6. A process according to claim 1 wherein the succinic anhydride ester alkyl group consists of between 1 and 4 carbon atoms.

7. A process according to claim 1 wherein the catalyst employed is copper and zinc oxide based, and consists of between 20 and 35% copper, and between 20 and 40% zinc.

8. A process according to claim 7, wherein the catalyst has both its components in their unreduced forms.

9. A process according to claim 7 wherein the catalyst has a surface area which is not any smaller than 30 $m^2g^{-1}$.

10. A process according to claim 1 wherein a stabilised copper chromite catalyst is employed, which consists of between 40 and 50% copper oxide, of between 40 and 50% chromium oxide, of between 5 and 15% barium or manganese oxide.

11. A process according to claim 10, wherein the catalyst has all its components in their unreduced forms.

12. A process according to claim 10 wherein the catalyst has a surface area which is not any smaller than 20 $m^2g^{-1}$.

13. A process according to claim 1 wherein the hydrogen and shot ester mixture in the shot contact the catalyst at an overall liquid hourly space velocity ranging between 0.1 and 1.0 $hr^{-1}$.

14. A process according to claim 13 wherein the reaction is carried out at an overall liquid hourly space velocity that ranges between 0.2 and 0.4 $hr^{-1}$.

* * * * *